(12) United States Patent
Daynes et al.

(10) Patent No.: US 8,676,312 B2
(45) Date of Patent: Mar. 18, 2014

(54) MEDICAL DEVICES ALERTING USER ABOUT POTENTIAL INTERRUPTION OF WIRELESS PATIENT DATA TRANSFER

(75) Inventors: John Carlton Daynes, Redmond, WA (US); Nathan Woodruff Daynes, Snoqualmie, WA (US)

(73) Assignee: Physio-Control, Inc., Redmond, WA (US)

( * ) Notice: Subject to any disclaimer, the term of this patent is extended or adjusted under 35 U.S.C. 154(b) by 105 days.

(21) Appl. No.: 13/284,610

(22) Filed: Oct. 28, 2011

(65) Prior Publication Data
US 2012/0296384 A1 Nov. 22, 2012

Related U.S. Application Data

(60) Provisional application No. 61/487,849, filed on May 19, 2011.

(51) Int. Cl.
*A61N 1/362* (2006.01)
(52) U.S. Cl.
USPC .................................. 607/5; 607/32; 607/60
(58) Field of Classification Search
USPC .................. 607/5–8, 31, 32, 59, 60
See application file for complete search history.

(56) References Cited

U.S. PATENT DOCUMENTS

| 6,141,584 | A | 10/2000 | Rockwell et al. | |
|---|---|---|---|---|
| 2004/0127774 | A1* | 7/2004 | Moore et al. | 600/300 |
| 2006/0161214 | A1* | 7/2006 | Patel | 607/32 |

FOREIGN PATENT DOCUMENTS

| WO | 2004/061704 A2 | 7/2004 |
|---|---|---|
| WO | 2008/060197 A1 | 5/2008 |

OTHER PUBLICATIONS

International Search Report, Patent Cooperation Treaty, Jul. 17, 2012, 14 pages, PCT/US2012/032700, European Patent Office, Rijswijk, Netherlands.

* cited by examiner

*Primary Examiner* — Eric D. Bertram
(74) *Attorney, Agent, or Firm* — Marger Johnson & McCollom PC

(57) ABSTRACT

An external defibrillator can receive wirelessly a data signal transmitted by a transmitting device over a communication link. The defibrillator can include a processor configured to monitor a reception parameter of the communication link while the data signal is being received and to set an alert flag if the processor determines from the reception parameter that reception of the data signal may be discontinued prematurely. The defibrillator can also include a user interface capable of outputting an alerting user notification responsive to the alert flag being set.

28 Claims, 10 Drawing Sheets

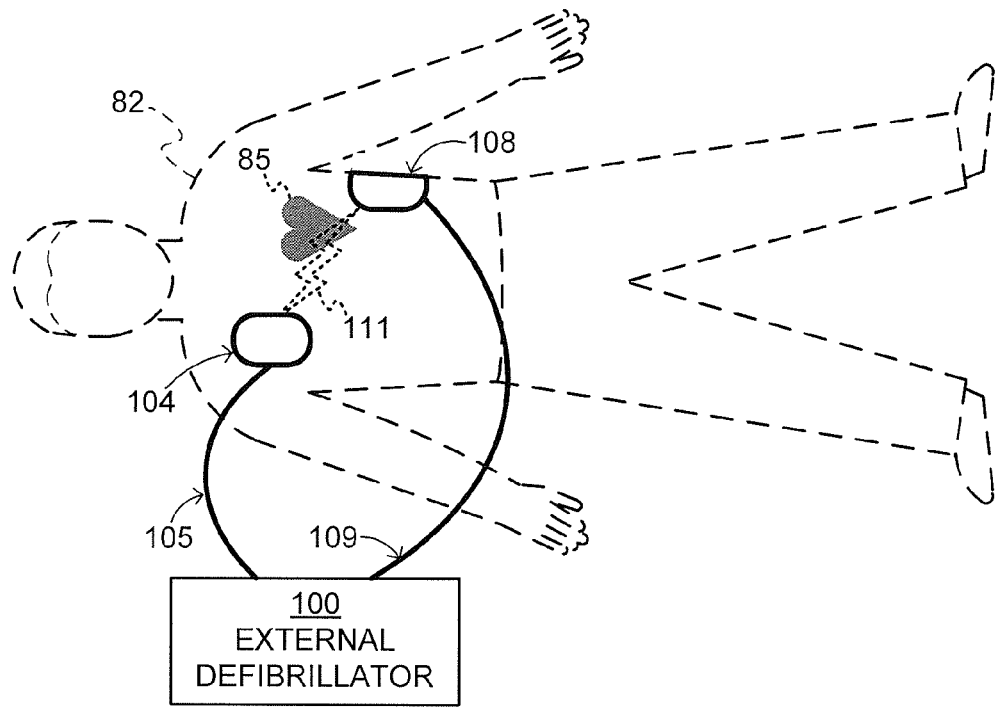
FIG. 1  *DEFIBRILLATION SCENE*
| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |
FIG. 2  *TWO MAIN TYPES OF EXTERNAL DEFIBRILLATORS*

COMPONENTS OF EXTERNAL DEFIBRILLATOR

COMLINK ESTABLISHED BETWEEN
EXTERNAL DEFIBRILLATOR AND
TRANSMITTING DEVICE

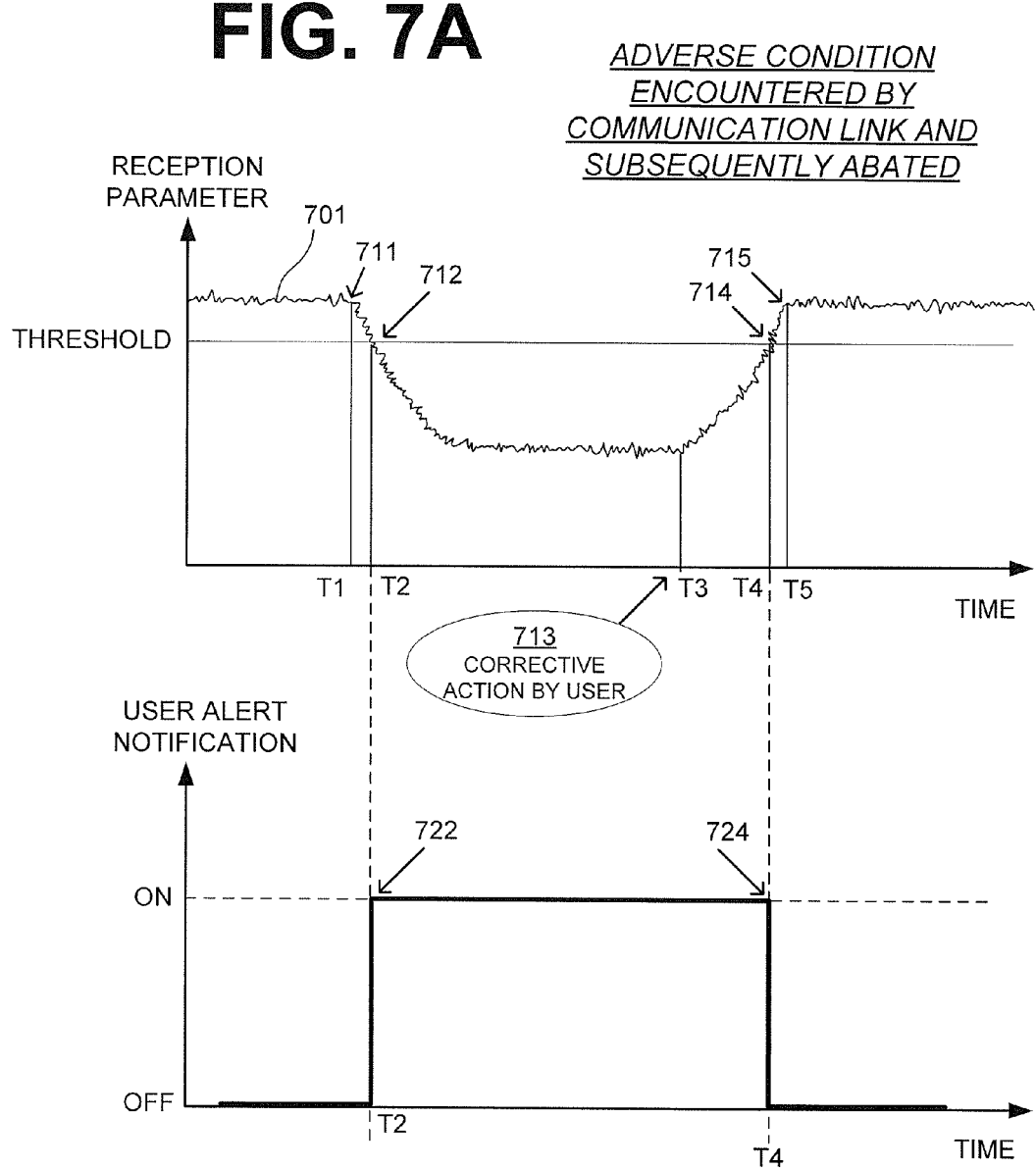

*METHODS OF USER INTERACTING WITH EXTERNAL DEFIBRILLATOR*

MEDICAL DEVICES ALERTING USER ABOUT POTENTIAL INTERRUPTION OF WIRELESS PATIENT DATA TRANSFER

RELATIONSHIP WITH OTHER APPLICATIONS

This patent application claims priority from U.S.A. Provisional Patent Application Ser. No. 61/487,849, entitled DEVICES PREVENTING INTERRUPTION OF WIRELESS PATIENT DATA TRANSFER, filed on May 19, 2011, the disclosure of which is hereby incorporated by reference for all purposes.

This patent application may be found to be related to U.S. patent application Ser. No. [SER_NO_OF_7257-0036/P40442.01], entitled MANUALLY INITIATING WIRELESS RECEPTION OF RESUSCITATION EVENT DATA FROM MEDICAL DEVICE, assigned to the same assignee, filed on Jul. 26, 2011.

This patent application may be found to be related to U.S. patent application Ser. No. [SER_NO_OF_7257-0039/P40442.02], entitled MANUALLY INITIATING WIRELESS TRANSMISSION OF RESUSCITATION EVENT DATA TO MEDICAL DEVICE, assigned to the same assignee, filed on Jul. 26, 2011.

FIELD

This invention generally relates to the field of medical devices such as defibrillators.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body.

The heart chambers pump because of the heart's electrical control system. More particularly, the sinoatrial (SA) node generates an electrical impulse, which generates further electrical signals. These further signals cause the above-described contractions of the various chambers in the heart, in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and, if not treated, death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, they will die soon, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF or other heart arrythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because blood flow has stopped. They should receive therapy quickly.

For a VF victim without an ICD, a different type of defibrillator can be used, which is called an external defibrillator. External defibrillators have been made portable, so they can be brought to a potential VF victim quickly enough to revive them.

During VF, the person's condition deteriorates, because the blood is not flowing to the brain, heart, lungs, and other organs. Blood flow must be restored, if resuscitation attempts are to be successful.

Cardiopulmonary Resuscitation (CPR) is one method of forcing blood flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows the deterioration that would otherwise occur while a defibrillator is being retrieved. Indeed, for patients with an extended down-time, survival rates are higher if CPR is administered prior to defibrillation.

Advanced medical devices can actually coach a rescuer who performs CPR. For example, a medical device can issue instructions, and even prompts, for the rescuer to perform CPR more effectively.

BRIEF SUMMARY

The present description gives instances of medical devices, software and methods, the use of which may help overcome problems and limitations of the prior art.

In some embodiments, an external defibrillator may establish a communication link ("comlink") with a transmitting device and receive a data signal from the transmitting device over the comlink. The defibrillator may optionally decode and store resuscitation event data from the received data signal. The defibrillator may monitor a reception parameter of the comlink while the data signal is being received and, responsive to a determination from the reception parameter that the reception of the data signal may be discontinued prematurely, set an alert flag. The defibrillator may output an alerting user notification responsive to the alert flag being set.

In some embodiments, an external defibrillator may start receiving wirelessly a data signal encoding resuscitation event data from a transmitting device that is distinct from the defibrillator. After the receiving starts, the defibrillator may provide an alert that reception of the data signal may be discontinued prematurely. Responsive to being so alerted, a user may investigate whether there is an adverse condition affecting the reception and, if so, the user may cause the condition to be abated.

An advantage over the prior art is that a data signal encoding resuscitation event data, for example, may be transferred wirelessly without interruption to an external defibrillator from a transmitting device. Indeed, should a condition occur that is potentially adverse to the wireless communication, the user will have been alerted and can hopefully abate the condition.

These and other features and advantages of this description will become more readily apparent from the following Detailed Description, which proceeds with reference to the drawings, in which:

BRIEF DESCRIPTION OF THE DRAWINGS

FIG. 1 is a diagram of a scene where an external defibrillator is used to save the life of a person according to embodiments.

FIG. 2 is a table listing two main types of the external defibrillator shown in FIG. 1, and who they might be used by.

FIG. 7A is a time diagram of a reception parameter corresponding to a communication link between an external defibrillator and a transmitting device encountering an adverse condition that is subsequently abated according to embodiments.

FIG. 7B is a time diagram of a user alert notification that is issued and subsequently stopped responsive to the communication link between the external defibrillator and the transmitting device of FIG. 7A encountering the adverse condition that is subsequently abated according to embodiments.

DETAILED DESCRIPTION

Figure 3:
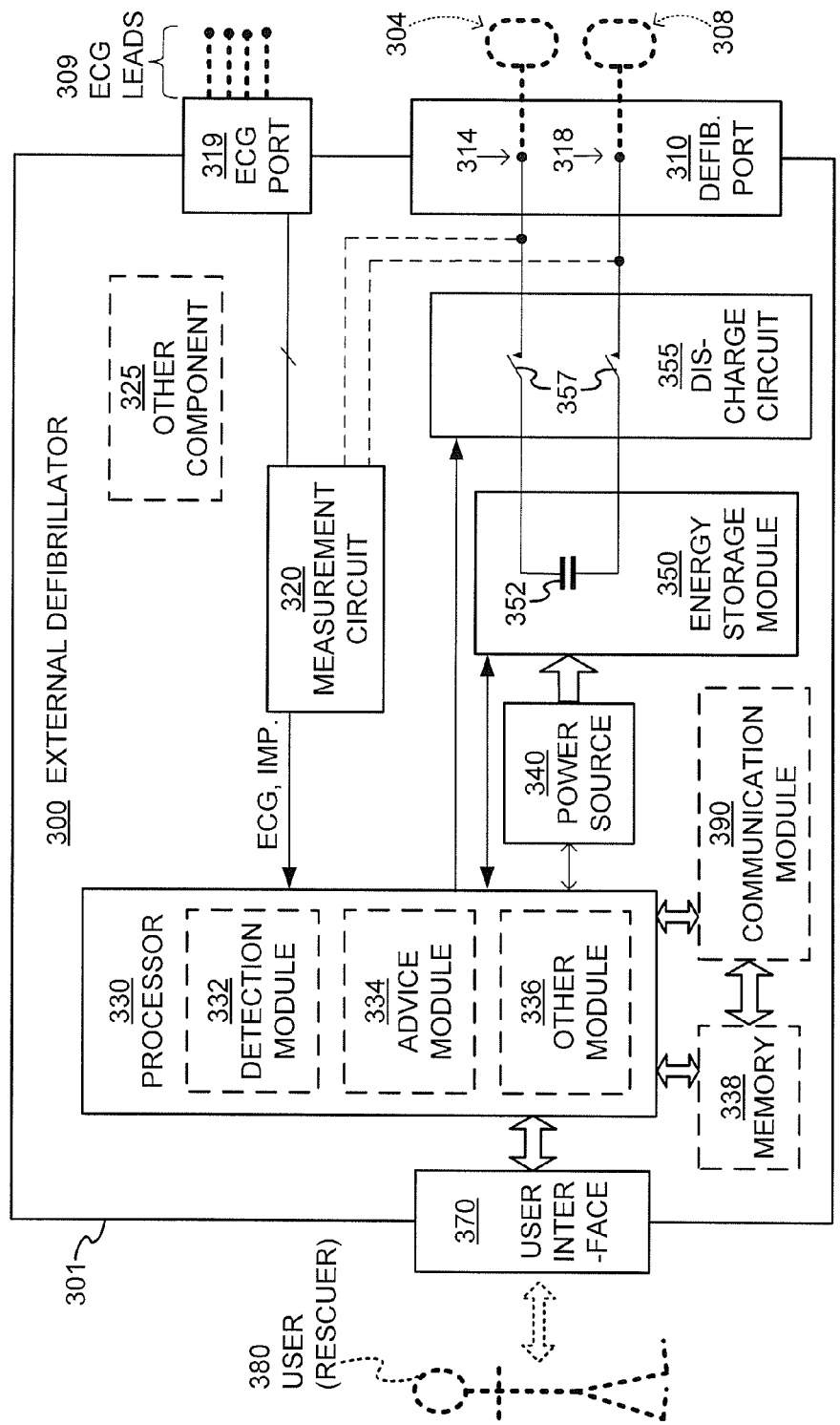
FIG. 3 is a functional block diagram showing components of an external defibrillator, such as the one shown in FIG. 1, which is made according to embodiments.

FIG. 1 is a diagram of a defibrillation scene. A person 82 is lying on their back. Person 82 could be a patient in a hospital, or someone found unconscious, and then turned to be on their back. Person 82 is experiencing a condition in their heart 85, which could be Ventricular Fibrillation (VF).

A portable external defibrillator 100 has been brought close to person 82. At least two defibrillation electrodes 104, 108 are usually provided with external defibrillator 100, and are sometimes called electrodes 104, 108. Electrodes 104, 108 are coupled with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, goes also through heart 85, in an attempt to restart it, for saving the life of person 82.

Defibrillator 100 can be one of different types, each with different sets of features and capabilities. The set of capabilities of defibrillator 100 is determined by planning who would use it, and what training they would be likely to have. Examples are now described.

FIG. 2 is a table listing two main types of external defibrillators, and who they are primarily intended to be used by. A first type of defibrillator 100 is generally called a defibrillator-monitor, because it is typically formed as a single unit in combination with a patient monitor. A defibrillator-monitor is sometimes called monitor-defibrillator. A defibrillator-monitor is intended to be used by persons in the medical professions, such as doctors, nurses, paramedics, emergency medical technicians, etc. Such a defibrillator-monitor is intended to be used in a pre-hospital or hospital scenario.

As a defibrillator, the device can be one of different varieties, or even versatile enough to be able to switch among different modes that individually correspond to the varieties.

One variety is that of an automated defibrillator, which can determine whether a shock is needed and, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological indicators of a person in an emergency scenario. These physiological indicators are typically monitored as signals. For example, these signals can include a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is more critically being deployed at an Intensive Care Unit, and so on.

AEDs, however, can also be used by people who are not in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Indeed, the people who will first reach the VF sufferer may not be in the medical professions.

Increasing awareness has resulted in AEDs being deployed in public or semi-public spaces, so that even a member of the public can use one, if they have obtained first aid and CPR/AED training on their own initiative. This way, defibrillation can be administered soon enough after the onset of VF, to hopefully be effective in rescuing the person.

There are additional types of external defibrillators, which are not listed in FIG. 2. For example, a hybrid defibrillator can have aspects of an AED, and also of a defibrillator-monitor. A usual such aspect is additional ECG monitoring capability.

FIG. 3 is a diagram showing components of an external defibrillator 300 made according to embodiments. These components can be, for example, in external defibrillator 100 of FIG. 1. Plus, these components of FIG. 3 can be provided in a housing 301, which is also known as casing 301.

External defibrillator 300 is intended for use by a user 380, who would be the rescuer. Defibrillator 300 typically includes a defibrillation port 310, such as a socket in housing 301. Defibrillation port 310 includes nodes 314, 318. Defibrillation electrodes 304, 308, which can be similar to electrodes 104, 108, can be plugged in defibrillation port 310, so as to make electrical contact with nodes 314, 318, respectively. It is also possible that electrodes can be connected continuously to defibrillation port 310, etc. Either way, defibrillation port 310 can be used for guiding via electrodes to person 82 an electrical charge that has been stored in defibrillator 300, as will be seen later in this document.

If defibrillator 300 is actually a defibrillator-monitor, as was described with reference to FIG. 2, then it will typically also have an ECG port 319 in housing 301, for plugging in ECG leads 309. ECG leads 309 can help sense an ECG signal, e.g. a 12-lead signal, or from a different number of leads. Moreover, a defibrillator-monitor could have additional ports (not shown), and an other component 325 for the above described additional features, such as patient signals.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at advice based on outputs of detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 300 may further issue prompts for it, and so on.

Processor 330 can include additional modules, such as module 336, for other functions. In addition, if other component 325 is indeed provided, it may be operated in part by processor 330, etc.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for user 380, etc. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes one or more capacitors 352, and so on.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and so on.

Defibrillator 300 further includes a user interface 370 for user 380. User interface 370 can be made in any number of ways. For example, interface 370 may include a screen, to display what is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on.

Figure 4:
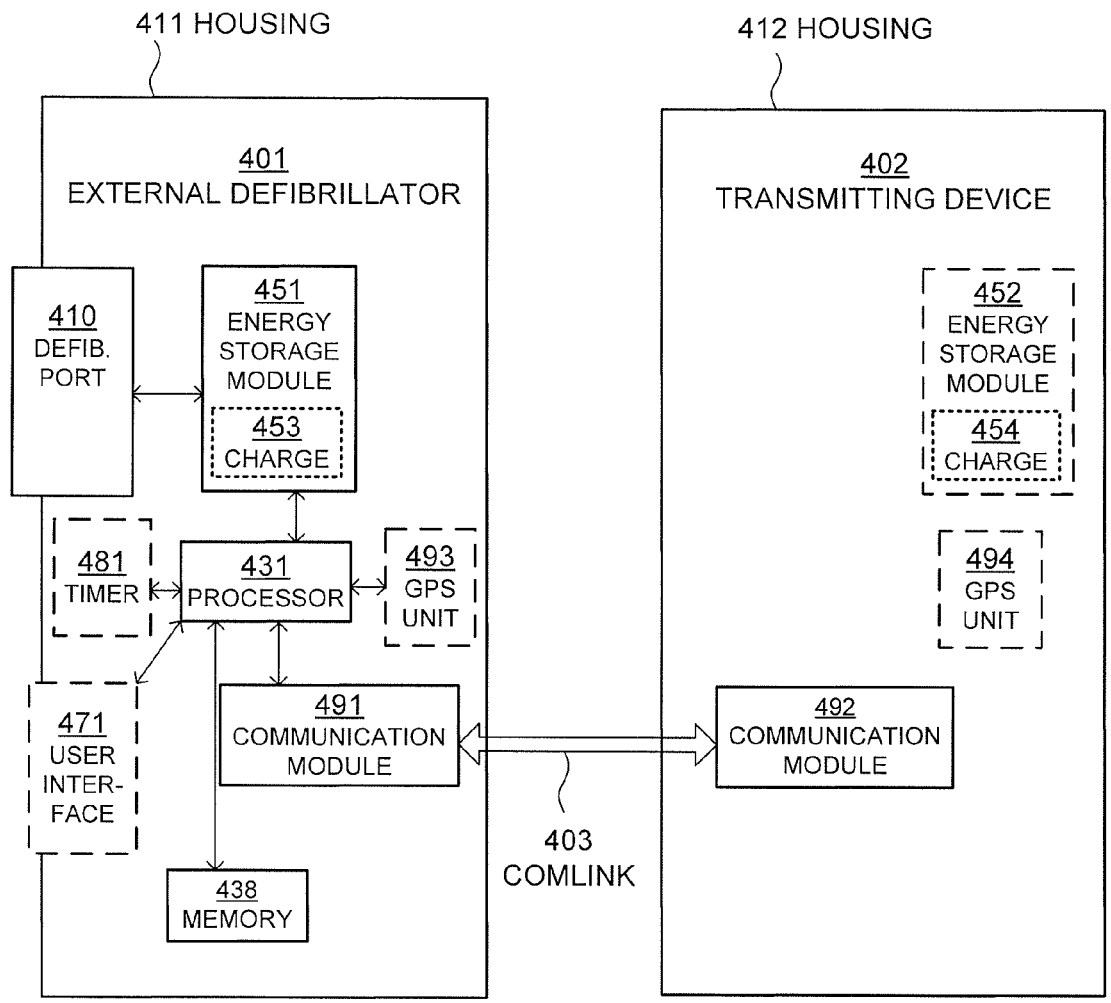
FIG. 4 is a diagram showing a communication link established between an external defibrillator and a transmitting device according to embodiments.

FIG. 4 is a diagram showing a wireless communication link ("comlink") 403 that is established between an external defibrillator 401 for defibrillating a person, and for receiving resuscitation event data from a transmitting device 402 distinct from the defibrillator 401, and the transmitting device 402, according to embodiments. A user may facilitate the defibrillator 401 to start receiving the resuscitation event data from the transmitting device 402 over the comlink. After the receiving starts, the defibrillator 401 may alert the user that reception of the data signal may be discontinued prematurely. Responsive to being so alerted, the user may investigate whether there is an adverse condition affecting the reception and abate the adverse condition.

The defibrillator 401 includes a first housing 411, an energy storage module 451 in an interior of the first housing 411 for storing an electrical charge 453, and a defibrillation port 410 for guiding via electrodes the electrical charge 453 to a person, such as the person 82 of FIG. 1.

The transmitting device 402 includes a second housing 412 and a second wireless communication module 492. In certain embodiments, the transmitting device 402 also includes a second energy storage module 452 in an interior of the second housing 412 for storing an electrical charge 454. For example, the transmitting device 402 may be a second external defibrillator distinct from the defibrillator 401.

The defibrillator 401 also includes a first wireless communication module 491 for establishing the wireless comlink 403 with the second communication module 492. The first communication module 491 is further adapted to receive wirelessly a data signal transmitted by the second communication module 492 over the comlink 403. In certain embodiments, the data signal encodes resuscitation event data stored in the transmitting device 402. The defibrillator 401 further includes a memory 438 that is adapted to store the resuscitation event data that has been decoded from the data signal.

The defibrillator 401 includes a processor 431 that is configured to monitor a reception parameter of the comlink 403 while the data signal is being received. Any number of parameters can be used. The processor 431 is also configured to set an alert flag if the processor 431 determines from the reception parameter that reception of the data signal may be discontinued prematurely. In addition, the flag may be implemented in any number of ways.

The defibrillator optionally includes a user interface 471 that is capable of outputting an alerting user notification responsive to the alert flag being set. In certain embodiments, the user interface 471 is further capable of outputting a regular user notification that is different from the alerting user notification that the data signal is being received. The alerting user notification may be at least one of a visual, audio, or physical notification. The alerting user notification may further include a suggestion that a user check whether the transmitting device 402 has been moved away from the defibrillator 401. Alternatively or in addition thereto, the alerting user notification may include a suggestion that a user check for a potential source of interference with the communication link.

In certain embodiments, the reception parameter includes a data rate of the data signal being received over the communication link, and the alert flag is set if the data rate is decreased below a data rate threshold. In other embodiments, the reception parameter includes a Received Signal Strength Indicator (RSSI) of the data signal, and the alert flag is set if the RSSI crosses below an RSSI threshold. In yet other embodiments, the reception parameter includes a rate of change of an RSSI of the data signal, and the alert flag is set if the rate of change crosses a threshold.

In certain embodiments, the reception parameter includes an Error Correction Rate (ECR) derived from correcting errors as the resuscitation event data is decoded from the data signal, and the alert flag is set if the ECR increases above an ECR threshold. In other embodiments, the reception parameter includes a rate of change of an ECR from correcting errors as the resuscitation event data is decoded from the data signal, and the alert flag is set if the rate of change crosses a threshold.

In certain embodiments, the processor 431 is further configured to reset the alert flag if the processor 431 determines from the reception parameter that the reception of the data signal has been restored. In these embodiments, the user interface 471 may be further capable of outputting a regular user notification different from the alerting user notification that the data signal is being received responsive to the determination that the reception of the data signal has been restored.

In certain embodiments, the processor 431 is further configured to determine an expected amount of time needed for the first communication module 491 to fully receive the data signal, and determine an expected amount of time remaining before the receiving of the data signal becomes discontinued. The processor 431 may interact with an optional timer 481 in these embodiments. The processor 431 may be configured to determine the expected amount of time needed for the first communication module 491 to fully receive the data signal by determining an amount of data remaining to be received. Alternatively or in addition thereto, the processor 431 may be configured to determine the expected amount of time remaining before the receiving of the data signal becomes discontinued by determining a degradation rate of the communication link.

The processor 431 may be configured to not set the alert flag if the processor 431 determines that the expected amount of time needed for the first communication module 491 to fully receive the data signal is less than the expected amount of time remaining before the receiving of the data signal becomes discontinued. The alerting user notification may be structured to convey the expected amount of time needed for the first communication module 491 to fully receive the data signal, or the expected amount of time remaining before the receiving of the data signal becomes discontinued, or both, to a user.

In certain embodiments, the defibrillator 401 further includes a GPS unit 493. Alternatively or in addition thereto, the transmitting device 402 may include a second GPS unit 494.

Figure 5A:
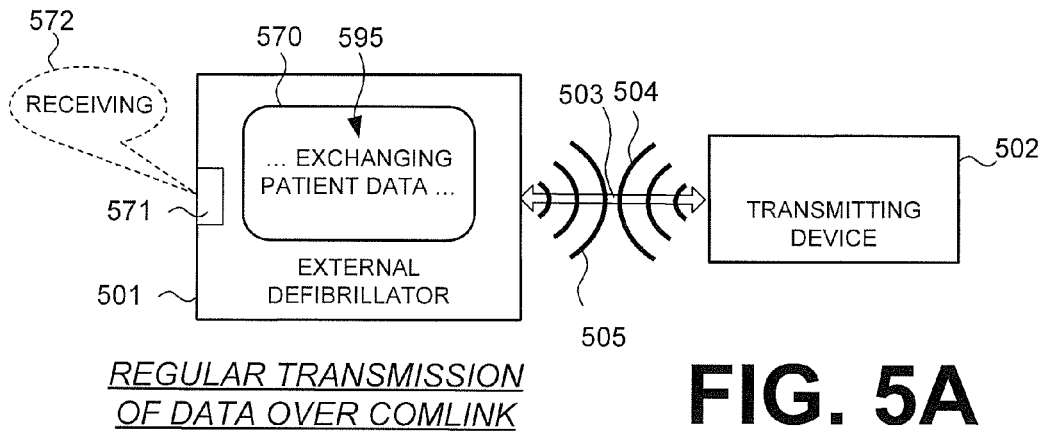
FIG. 5A is a diagram showing regular transmission of data over a communication link between an external defibrillator and a transmitting device according to embodiments.
Figure 5B:
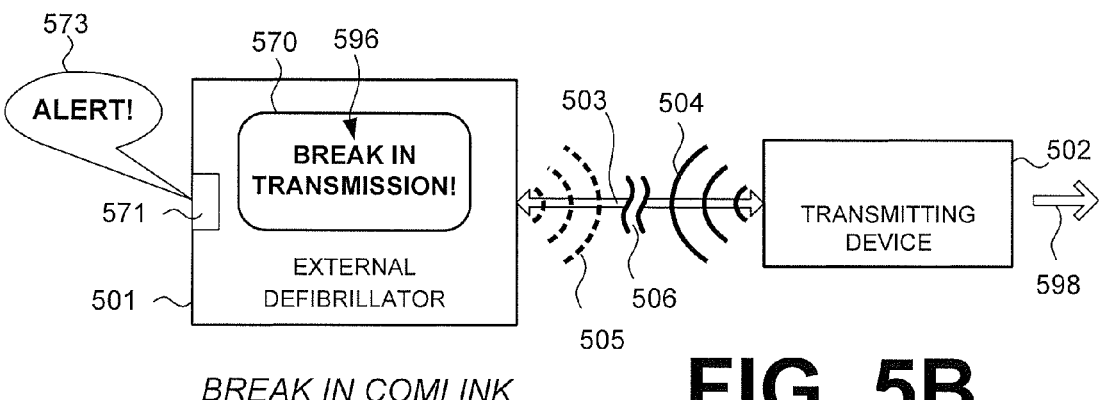
FIG. 5B is a diagram showing a break in the communication link between the external defibrillator and the transmitting device of FIG. 5A according to embodiments.
Figure 5C:
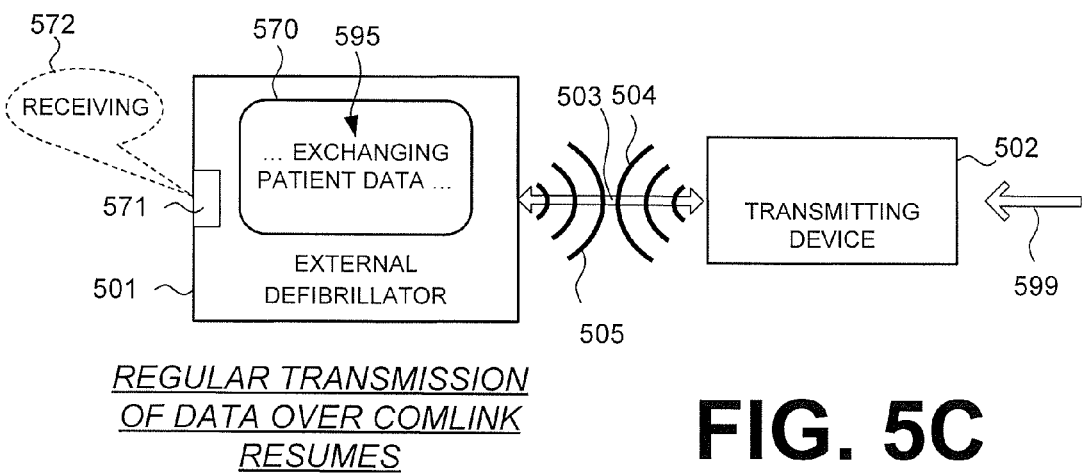
FIG. 5C is a diagram showing the regular transmission of data over the communication link between the external defibrillator and the transmitting device of FIG. 5B resuming according to embodiments.

FIGS. 5A-5C illustrate interactions between an external defibrillator 501 and a transmitting device 502, such as the external defibrillator 401 and transmitting device 402 of FIG. 4, respectively, according to embodiments.

FIG. 5A is a diagram showing regular transmission of data over a communication link ("comlink") 503 between the defibrillator 501 and the transmitting device 502 according to embodiments. The transmitting device 502 is transmitting a data signal to the defibrillator 501 over the comlink 503, as indicated by 504. The defibrillator 501 is receiving the data signal over the comlink 503, as indicated by 505. The data signal may encode resuscitation event data about a person being resuscitated, for example.

The defibrillator 501 has a user interface 571, such as the user interface 471 of FIG. 4. In certain embodiments, the user interface 571 may output a regular user audible notification 572 that the data signal is being received. Alternatively or in addition thereto, the defibrillator 501 may have a display 570 that is configured to output a regular user visual notification 595 that the data signal is being received.

FIG. 5B is a diagram showing a break 506 in the comlink 503 between the defibrillator 501 and the transmitting device 502 of FIG. 5A according to embodiments. While the transmitting device 502 continues to transmit, as indicated by 504, the defibrillator 501 no longer receives the data signal over the comlink 503, as indicated by 505. The break 506 may be a result of the transmitting device 502 being moved away from the defibrillator 501, as indicated by 598, for example.

The user interface 571 is configured to output an alerting user audible notification 573 responsive to the break 506. Alternatively or in addition thereto, the display 570 may be configured to output an alerting user visual notification 596 responsive to the break 506. Either or both of the alerting user audible notification 573 and visual notification 596 may include a suggestion that a user check whether the transmitting device 502 is being moved away from the defibrillator 501.

FIG. 5C is a diagram showing the regular transmission of data over the comlink 503 between the defibrillator 501 and the transmitting device 502 of FIG. 5B resuming, as indicated by 504 and 505, according to embodiments. For example, in situations where the break 506 in FIG. 5B was a result of the transmitting device 502 being moved away from the defibrillator 501, the resuming of the regular transmission of data may be a result of the transmitting device 502 being moved closer to the defibrillator 501, as indicated by 599.

In certain embodiments, the user interface 571 may output the regular user audible notification 572 that the data signal is being received. Alternatively or in addition thereto, the display 570 may be configured to output the regular user visual notification 595 that the data signal is being received.

Figure 6A:
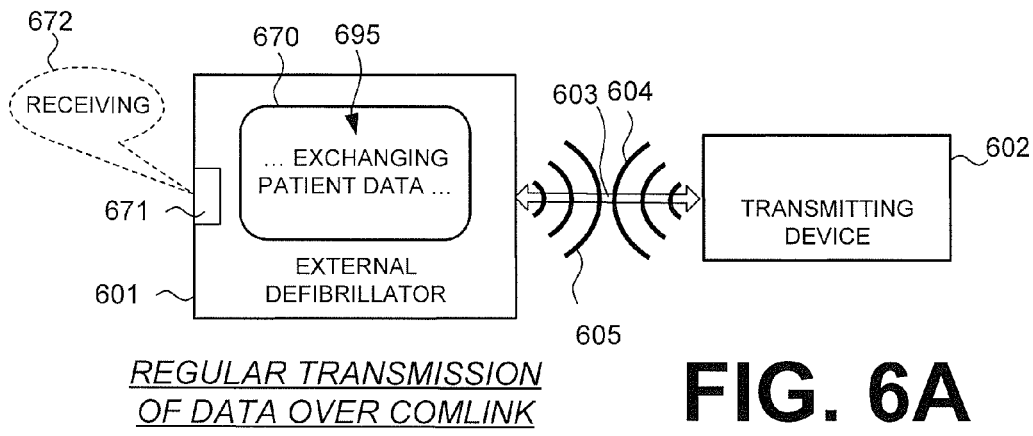
FIG. 6A is a diagram showing regular transmission of data over a communication link between an external defibrillator and a transmitting device according to embodiments.
Figure 6B:
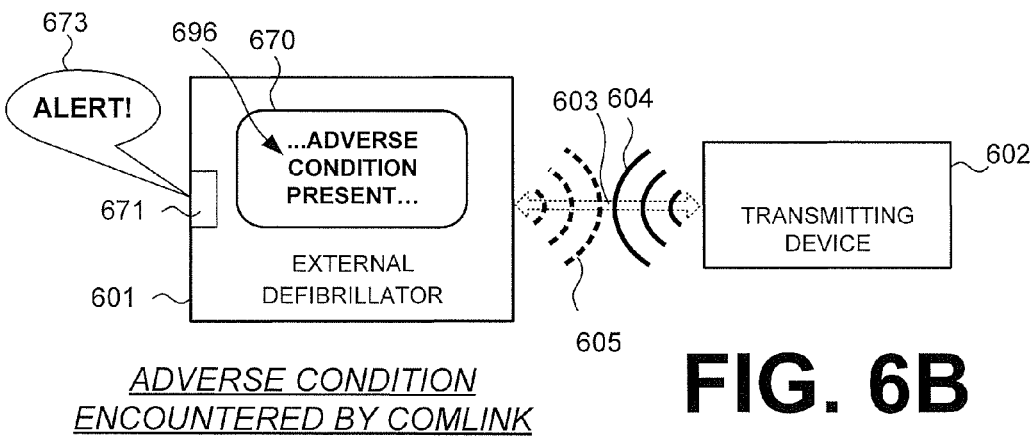
FIG. 6B is a diagram showing the communication link between the external defibrillator and the transmitting device of FIG. 6A encountering an adverse condition that may have an adverse impact on the transmission of data according to embodiments.
Figure 6C:
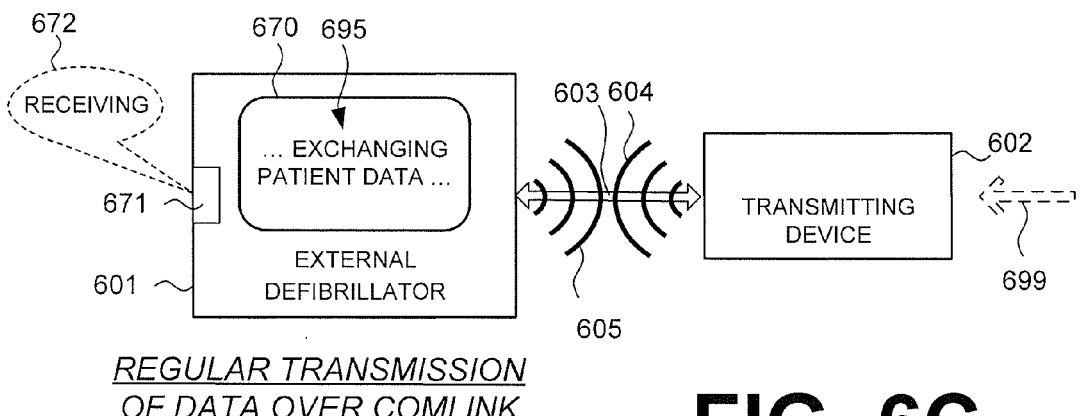
FIG. 6C is a diagram showing the regular transmission of data over the communication link between the external defibrillator and the transmitting device of FIG. 6B subsequent to the comlink encountering the adverse condition according to embodiments.

FIGS. 6A-6C illustrate interactions between an external defibrillator 601 and a transmitting device 602, such as the external defibrillator 401 and transmitting device 402 of FIG. 4, respectively, according to embodiments.

FIG. 6A is a diagram showing regular transmission of data over a communication link ("comlink") 603 between the defibrillator 601 and the transmitting device 602 according to embodiments. The transmitting device 602 is transmitting a data signal to the defibrillator 601 over the comlink 603, as indicated by 604. The defibrillator 601 is receiving the data signal over the comlink 603, as indicated by 605. The data signal may encode resuscitation event data about a person being resuscitated, for example.

The defibrillator 601 has a user interface 671, such as the user interface 471 of FIG. 4. In certain embodiments, the user interface 671 may output a regular user audible notification 672 that the data signal is being received. Alternatively or in addition thereto, the defibrillator 601 may have a display 670 that is configured to output a regular user visual notification 695 that the data signal is being received.

FIG. 6B is a diagram showing the comlink 603 between the defibrillator 601 and the transmitting device 602 of FIG. 6A encountering an adverse condition that may have an adverse impact on the transmission of data according to embodiments. While the transmitting device 602 continues to transmit, as indicated by 604, the defibrillator 601 no longer receives the data signal over the comlink 603, as indicated by 605. The adverse condition may be an incipient condition and may be a result of a source of interference, such as a medical device that is distinct from the defibrillator 601 and transmitting device 602 but is operating, e.g. transmitting, near or at the same frequency as one or both of the defibrillator 601 and transmitting device 602.

The user interface 671 is configured to output an alerting user audible notification 673 responsive to the adverse condition. Alternatively or in addition thereto, the display 670 may be configured to output an alerting user visual notification 696 responsive to the adverse condition. Either or both of the regular user audible notification 672 and visual notification 695 may include a suggestion that a user check for a potential source of interference with the comlink 603.

FIG. 6C is a diagram showing the regular transmission of data over the communication link between the external defibrillator and the transmitting device of FIG. 6B subsequent to the comlink encountering the adverse condition according to embodiments.

FIG. 6C is a diagram showing the regular transmission of data over the comlink 603 between the defibrillator 601 and the transmitting device 602 of FIG. 6B resuming, as indicated by 604 and 605, according to embodiments. For example, in situations where the adverse condition in FIG. 6B was a result of a source of interference, the resuming of the regular transmission of data may be a result of a user addressing the source of interference. In situations where the source of interference is a medical device distinct from the defibrillator 601 and transmitting device 602 but operating near or at the same frequency as one or both of the defibrillator 601 and transmitting device 602, the user may abate the adverse condition by either turning off the medical device or causing the medical device to operate at a different frequency by changing the channel, for example.

In certain embodiments, the user interface 671 may output the regular user audible notification 672 that the data signal is being received. Alternatively or in addition thereto, the display 670 may be configured to output the regular user visual notification 695 that the data signal is being received.

FIG. 7A is a time diagram of a reception parameter corresponding to a communication link ("comlink") between an external defibrillator and a transmitting device encountering an adverse condition that is subsequently abated according to embodiments. The reception parameter may correspond to a data rate of a data signal being received over the comlink, a Received Signal Strength Indicator (RSSI) of the data signal, or an Error Correction Rate (ECR) corresponding to the data signal, for example.

The monitored reception parameter is relatively stable and situated above a threshold before T1, as indicated by 701. At time T1, the reception parameter begins to fall, as indicated by 711. This change in the reception parameter is likely responsive to the comlink encountering an adverse condition. For example, there may be a potential source of interference affecting the comlink, a distance between the defibrillator and the transmitting device may be increasing, or both.

At time T2, the monitored reception parameter crosses the threshold, as indicated by 712. At this point, an alerting user notification may be issued by the defibrillator. Once corrective action is taken by the user at T3, as indicated by 713, the reception parameter begins to return to a restored condition. As described above, taking corrective action may include the user reducing a distance between the defibrillator and the transmitting device, turning off a potentially interfering device, changing the channel of a potentially interfering device, etc.

At time T4, the reception parameter crosses the threshold, as indicated by 714, until the reception parameter returns to approximately the same level as before T1 at T5, as indicated by 715. The reception parameter will generally remain at this level until another adverse condition is encountered or the monitoring of the reception parameter ceases.

FIG. 7B is a time diagram of a user alert notification that is issued and subsequently stopped responsive to the communication link ("comlink") between the external defibrillator and the transmitting device of FIG. 7A encountering the adverse condition that is subsequently abated according to embodiments. Until time T2, as indicated by 722, the monitored reception parameter of FIG. 7A is above the threshold. Once the reception parameter crosses the threshold at time T2, however, the user alert notification is issued. The user alert notification may provide one or more suggested actions for a user to abate an adverse condition that is potentially present, such as reducing the distance between the defibrillator and the transmitting device, turning off a potentially interfering device, changing the channel of a potentially interfering device, etc.

Until corrective action taken by the user causes the reception parameter of FIG. 7A to cross the threshold again at time T4, as indicated by 724, the user alert notification persists. After time T4, however, the user alert notification is stopped. No subsequent user alert notification will generally be issued unless the reception parameter crosses the threshold again.

The functions of this description may be implemented by one or more devices that include logic circuitry. The device performs functions and/or methods as are described in this document. The logic circuitry may include a processor that may be programmable for a general purpose, or dedicated, such as microcontroller, a microprocessor, a Digital Signal Processor (DSP), etc. For example, the device may be a digital computer like device, such as a general-purpose computer selectively activated or reconfigured by a computer program stored in the computer. Alternately, the device may be implemented by an Application Specific Integrated Circuit (ASIC), etc.

Moreover, methods are described below. The methods and algorithms presented herein are not necessarily inherently associated with any particular computer or other apparatus. Rather, various general-purpose machines may be used with programs in accordance with the teachings herein, or it may prove more convenient to construct more specialized apparatus to perform the required method steps. The required structure for a variety of these machines will become apparent from this description.

In all cases there should be borne in mind the distinction between methods in this description, and the method of operating a computing machine. This description relates both to methods in general, and also to steps for operating a computer and for processing electrical or other physical signals to generate other desired physical signals.

Programs are additionally included in this description, as are methods of operation of the programs. A program is generally defined as a group of steps leading to a desired result, due to their nature and their sequence. A program is usually advantageously implemented as a program for a computing machine, such as a general-purpose computer, a special purpose computer, a microprocessor, etc.

Storage media are additionally included in this description. Such media, individually or in combination with others, have stored thereon instructions of a program made according to the invention. A storage medium according to the invention is a computer-readable medium, such as a memory, and is read by the computing machine mentioned above.

Performing the steps or instructions of a program requires physical manipulations of physical quantities. Usually, though not necessarily, these quantities may be transferred, combined, compared, and otherwise manipulated or processed according to the instructions, and they may also be stored in a computer-readable medium. These quantities include, for example electrical, magnetic, and electromagnetic signals, and also states of matter that can be queried by such signals. It is convenient at times, principally for reasons of common usage, to refer to these quantities as bits, data bits, samples, values, symbols, characters, images, terms, numbers, or the like. It should be borne in mind, however, that all of these and similar terms are associated with the appropriate physical quantities, and that these terms are merely convenient labels applied to these physical quantities, individually or in groups.

This detailed description is presented largely in terms of flowcharts, display images, algorithms, and symbolic representations of operations of data bits within at least one computer readable medium, such as a memory. Indeed, such descriptions and representations are the type of convenient labels used by those skilled in programming and/or the data processing arts to effectively convey the substance of their work to others skilled in the art. A person skilled in the art of programming may use these descriptions to readily generate specific instructions for implementing a program according to the present invention.

Often, for the sake of convenience only, it is preferred to implement and describe a program as various interconnected distinct software modules or features, individually and collectively also known as software. This is not necessary, however, and there may be cases where modules are equivalently aggregated into a single program with unclear boundaries. In any event, the software modules or features of this description may be implemented by themselves, or in combination with others. Even though it is said that the program may be stored in a computer-readable medium, it should be clear to a person skilled in the art that it need not be a single memory, or even a single machine. Various portions, modules or features of it may reside in separate memories, or even separate machines. The separate machines may be connected directly, or through a network, such as a local access network (LAN), or a global network, such as the Internet.

It will be appreciated that some of these methods may include software steps that may be performed by different modules of an overall software architecture. For example, data forwarding in a router may be performed in a data plane, which consults a local routing table. Collection of performance data may also be performed in a data plane. The performance data may be processed in a control plane, which accordingly may update the local routing table, in addition to neighboring ones. A person skilled in the art will discern which step is best performed in which plane.

An economy is achieved in the present document in that a single set of flowcharts is used to describe both programs, and also methods. So, while flowcharts are described in terms of boxes, they can mean both method and programs.

For this description, the methods may be implemented by machine operations. In other words, embodiments of programs are made such that they perform methods of the invention that are described in this document. These may be optionally performed in conjunction with one or more human operators performing some, but not all of them. As per the above, the users need not be collocated with each other, but each only with a machine that houses a portion of the program. Alternately, some of these machines may operate automatically, without users and/or independently from each other.

Methods are now described.

Figure 8:
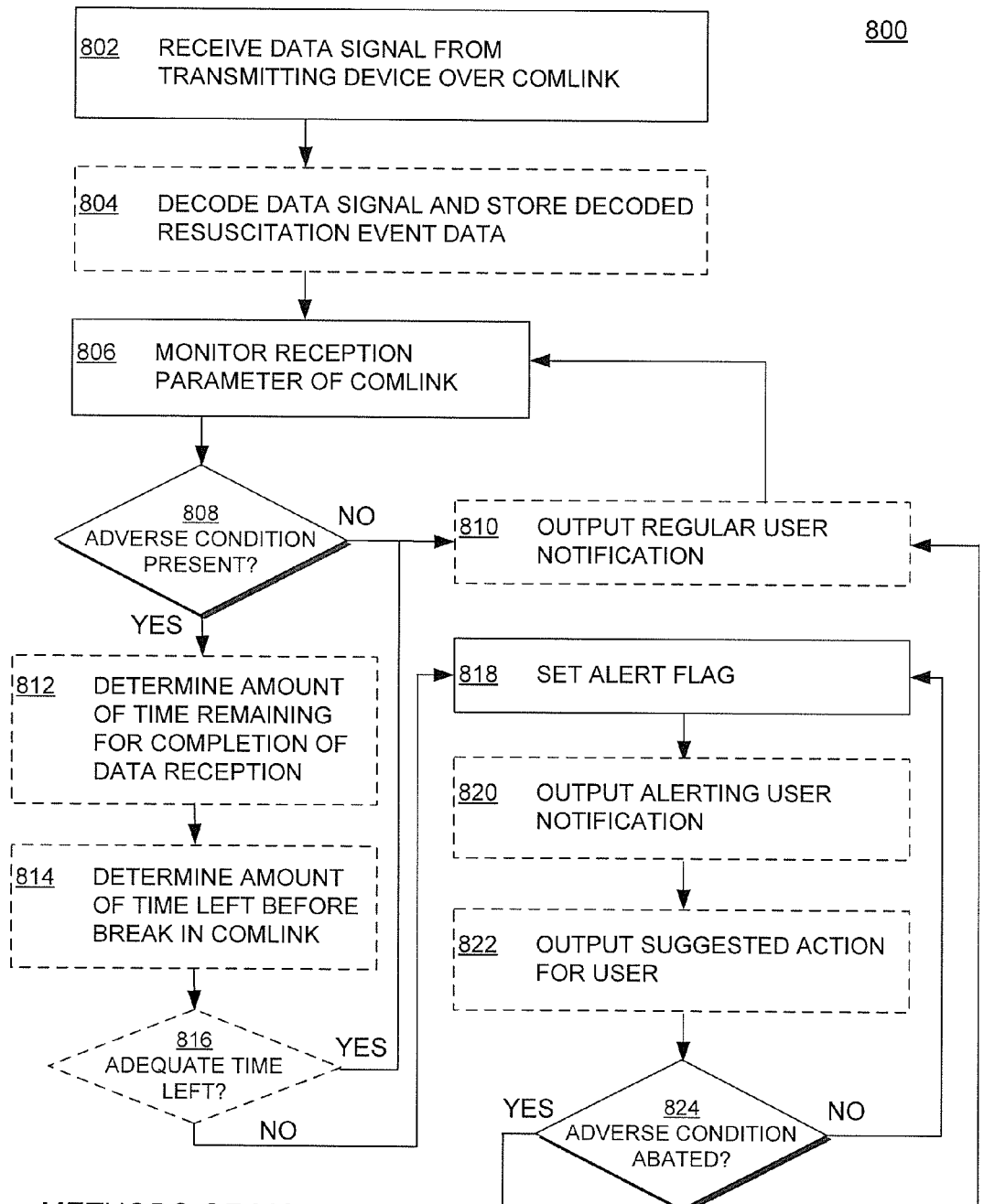
FIG. 8 is a flowchart for illustrating example methods executable by an external defibrillator receiving data from a transmitting device over a communication link according to embodiments.

FIG. 8 is a flowchart for illustrating example methods 800 executable by an external defibrillator receiving data from a transmitting device over a communication link ("comlink") established with the transmitting device according to embodiments. In an operation 802, a data signal is received from the transmitting device over the communication link that encodes resuscitation event data about a person being resuscitated. In an optional operation 804, the data signal is decoded and the decoded resuscitation event data is stored. The decoding may be performed during reception of the data or subsequent to completion of data reception. The decoded data may be stored in the defibrillator, in another device, or both.

In an operation 806, a reception parameter of the comlink is monitored while the data signal is being received. A determination is subsequently made as to whether an adverse condition is present, as indicated by 808. An operation 818 includes setting an alert flag responsive to a determination from the reception parameter that reception of the data signal may be discontinued prematurely. An optional operation 810 includes outputting a regular user notification different from the alerting user notification that the data signal is being received.

Responsive to a determination at 808 that an adverse condition is present, optional operations at 812 and 814 include, respectively, determining an estimated amount of time needed for the receiving of the data signal to complete and determining an estimated amount of time remaining before the receiving of the data signal is discontinued due to a break in the comlink, for example.

In a subsequent optional operation 816, a determination is made as to whether there is an adequate amount of time left for completion of the data reception. If so, the method 800 may return to the operation 806; otherwise, the method 800 advances to the operation 818, which is discussed above. In certain embodiments, the method 800 may advance to the optional operation 810 before returning to the operation 806.

An optional operation 820 includes outputting an alerting user notification responsive to the alert flag being set. Another optional operation 822 includes suggesting an action for a user. For example, the alerting user notification of 820 may include a suggestion that a user check whether the transmitting device is being moved away from the external defibrillator. Alternatively or in addition thereto, the alerting user notification of 820 may include a suggestion that a user check for a potential source of interference with the comlink.

The optional operation 810 may include suppressing the alerting user notification of 820 responsive to a determination that the estimated amount of time needed for the receiving of the data signal to complete is less than the estimated amount of time remaining before the receiving of the data signal is discontinued. In certain embodiments, the alerting user notification includes the estimated amount of time needed for the receiving of the data signal to complete and the estimated amounted of time remaining before the receiving of the data signal is discontinued.

In an operation 824, a determination is made as to whether the adverse condition has abated or been abated. If so, the method 800 may return to the operation 806; otherwise, the method 800 may advance to the operation 818, which is discussed above. In certain embodiments, the method 800 may advance to the optional operation 810 before returning to the operation 806. For example, the operation 810 may include outputting a regular user notification different from the alerting user notification that the data signal is being received responsive to a determination that the reception of the data signal has been restored.

Embodiments may further include defibrillating the person.

Figure 9:
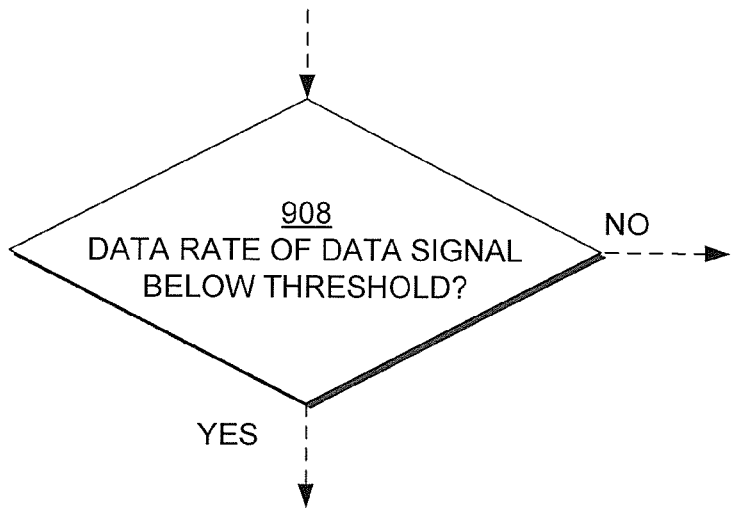
FIG. 9 is a flowchart for illustrating example methods executable by an external defibrillator evaluating a reception parameter of a communication link according to embodiments.

FIG. 9 is a flowchart for illustrating example methods executable by an external defibrillator evaluating a reception parameter of a communication link according to embodiments. In the operation 908, which represents at least a portion of the operation 808 of FIG. 8 in certain embodiments, the reception parameter, as monitored at operation 806 of FIG. 8, includes a data rate of the data signal being received over the communication link and the alert flag is set, at operation 818 of FIG. 8, if the data rate is decreased below a data rate threshold; otherwise, the method 800 of FIG. 8 may return to the operation 806. In certain embodiments, the method 800 may advance to the optional operation 810, discussed above, before returning to the operation 806.

Figure 10:
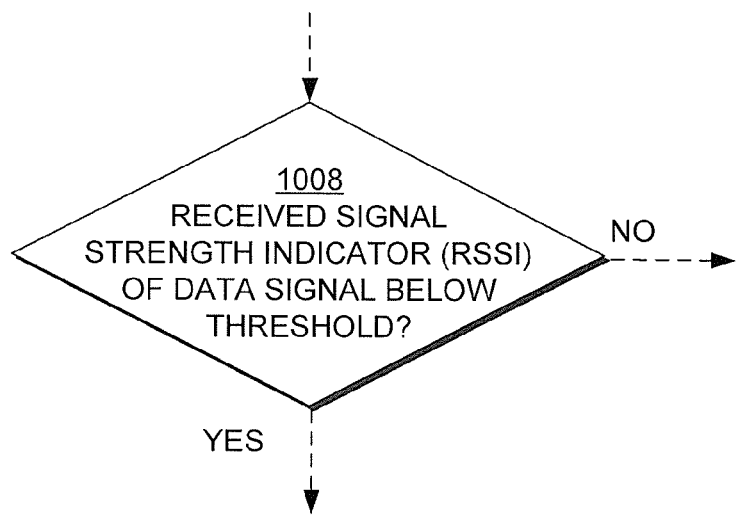
FIG. 10 is a flowchart for illustrating example methods executable by an external defibrillator evaluating a reception parameter of a communication link according to embodiments.

FIG. 10 is a flowchart for illustrating example methods executable by an external defibrillator evaluating a reception parameter of a communication link according to embodiments. In the operation 1008, which represents at least a portion of the operation 808 of FIG. 8 in certain embodiments, the reception parameter, as monitored at operation 806 of FIG. 8, includes a Received Signal Strength Indicator (RSSI) of the data signal and the alert flag is set, at operation 818 of FIG. 8, if the RSSI crosses below an RSSI threshold; otherwise, the method 800 of FIG. 8 may return to the operation 806. In certain embodiments, the method 800 may advance to the optional operation 810, discussed above, before returning to the operation 806.

Figure 11:
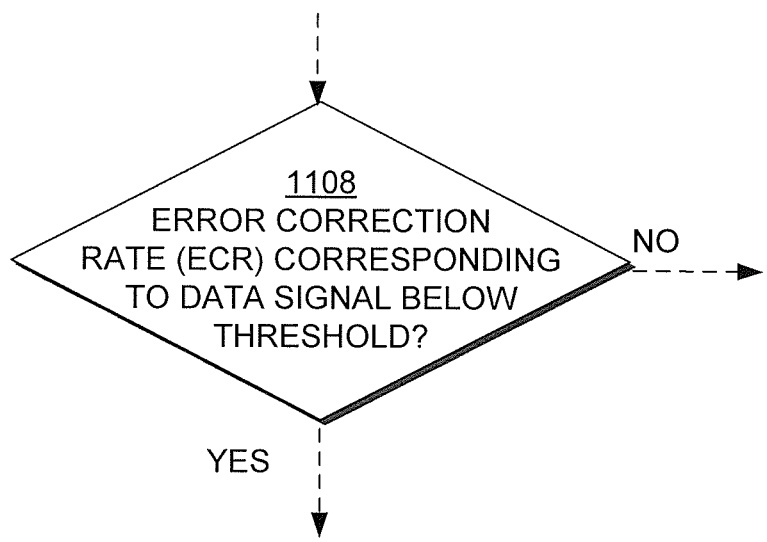
FIG. 11 is a flowchart for illustrating example methods executable by an external defibrillator evaluating a reception parameter of a communication link according to embodiments.

FIG. 11 is a flowchart for illustrating example methods executable by an external defibrillator evaluating a reception parameter of a communication link according to embodiments. In the operation 1108, which represents at least a portion of the operation 808 of FIG. 8 in certain embodiments, the reception parameter, as monitored at operation 806 of FIG. 8, includes an Error Correction Rate (ECR) from correcting errors as the resuscitation event data is decoded from the data signal and the alert flag is set, at operation 818 of FIG. 8, if the ECR increases above an ECR threshold; otherwise, the method 800 of FIG. 8 may return to the operation 806. In certain embodiments, the method 800 may advance to the optional operation 810, discussed above, before returning to the operation 806.

Figure 12:
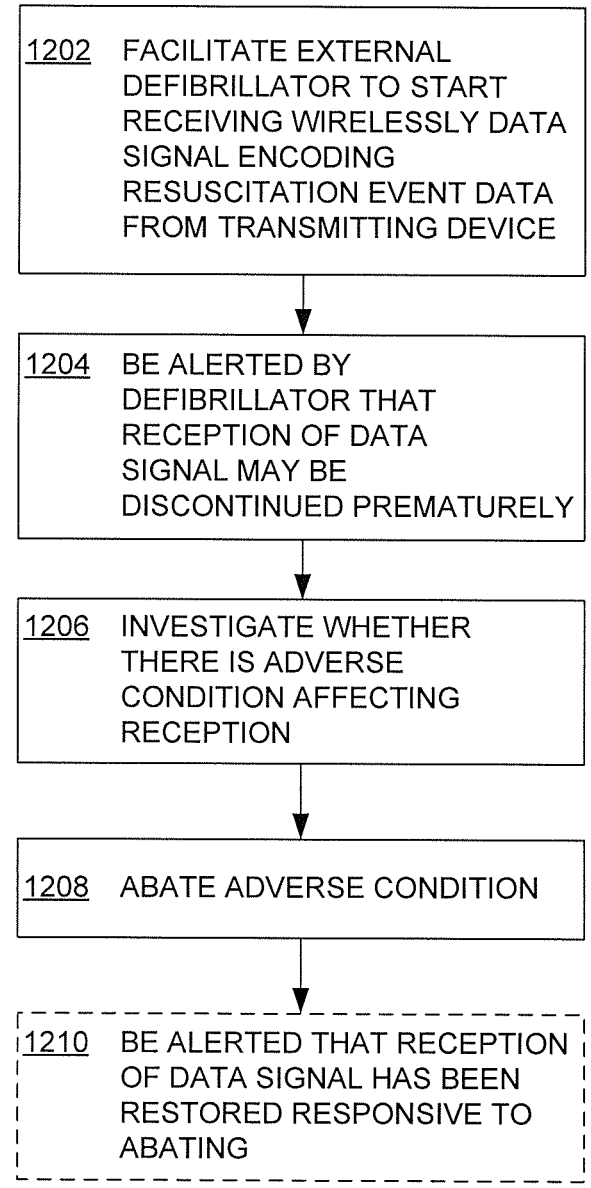
FIG. 12 is a flowchart for illustrating example methods of a user using an external defibrillator receiving data from a transmitting device over a communication link according to embodiments.

FIG. 12 is a flowchart for illustrating example methods 1200 of a user, such as a rescuer, using an external defibrillator receiving data from a transmitting device over a communication link according to embodiments. In each of the steps described below, the term "user" may refer to one or more persons and may or may not include the same person(s) for each step.

A step at 1202 includes the user facilitating an external defibrillator to start receiving wirelessly a data signal encoding resuscitation event data from a transmitting device distinct from the external defibrillator. The step at 1202 may include the defibrillator establishing a wireless communication link ("comlink") with the transmitting device.

After the receiving at 1202 starts, a step at 1204 includes the user being alerted by the defibrillator that reception of the data signal may be discontinued prematurely. In certain embodiments, the defibrillator suggests a check for a potential source of interference. Alternatively or in addition thereto, the defibrillator may suggest that the adverse condition is an incipient condition. Alternatively or in addition thereto, the defibrillator may suggest that a distance between the defibrillator and the transmitting device is increasing.

Responsive to being so alerted at 1204, a step at 1206 includes the user investigating whether there is an adverse condition affecting the reception. For example, the user may determine whether there is a potential source of interference, whether a distance between the defibrillator and the transmitting device is increasing, or both. The defibrillator may suggest that the adverse condition is a decrease in a data rate of the data signal, a decrease in a Received Signal Strength Indicator (RSSI) of the data signal, or an increase in an Error Correction Rate (ECR) related to the data signal.

The method 1200 further includes the user abating the adverse condition, as indicated at step 1208. In certain embodiments, abating the condition includes the user decreasing a distance between the defibrillator and the transmitting device. An optional step at 1210 includes the user being alerted by the defibrillator that the reception of the data signal has been restored responsive to the abating.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems.

The following claims define certain combinations and sub-combinations of elements, features, steps, and/or functions, which are regarded as novel and non-obvious. Additional claims for other combinations and sub-combinations may be presented in this or a related document.

What is claimed is:

1. An external defibrillator for defibrillating a person, and for receiving resuscitation event data from a transmitting device distinct from the external defibrillator, the transmitting device including a second housing and a second wireless communication module, the external defibrillator comprising:
    a first housing;
    an energy storage module in an interior of the first housing configured to store an electrical charge;
    a defibrillation port configured to guide via electrodes the electrical charge to the person;
    a first wireless communication module configured to establish a wireless communication link with the second communication module, the first communication module being further adapted to receive wirelessly a data signal transmitted by the second communication module over the communication link, the data signal encoding the resuscitation event data stored in the transmitting device;
    a memory configured to store the resuscitation event data that has been decoded from the data signal;
    a processor configured to monitor a reception parameter of the communication link while the data signal is being received, and to set an alert flag if the processor determines from the reception parameter that reception of the data signal may be discontinued prematurely; and
    a user interface configured to output an alerting user notification responsive to the alert flag being set, in which
        the reception parameter includes an Error Correction Rate (ECR) derived from correcting errors as the resuscitation event data is decoded from the data signal, and
        the alert flag is set if the ECR increases above an ECR threshold.

2. The external defibrillator of claim 1, in which the user interface is further capable of outputting a regular user notification different from the alerting user notification that the data signal is being received.

3. The external defibrillator of claim 1, in which the alerting user notification is at least one of a visual, audio, or physical notification.

4. The external defibrillator of claim 1, in which the alerting user notification further includes a suggestion that a user check whether the transmitting device has been moved away from the defibrillator.

5. The external defibrillator of claim 1, in which the alerting user notification further includes a suggestion that a user check for a potential source of interference with the communication link.

6. The external defibrillator of claim 1, in which the processor is further configured to reset the alert flag if the processor determines from the reception parameter that the reception of the data signal has been restored.

7. The external defibrillator of claim 6, in which the user interface is further capable of outputting a regular user notification different from the alerting user notification that the data signal is being received responsive to the determination that the reception of the data signal has been restored.

8. The external defibrillator of claim 1, in which
the transmitting device is a second external defibrillator distinct from the defibrillator.

9. An external defibrillator for defibrillating a person, and for receiving resuscitation event data from a transmitting device distinct from the external defibrillator, the transmitting device including a second housing and a second wireless communication module, the external defibrillator comprising:
a first housing;
an energy storage module in an interior of the first housing configured to store an electrical charge;
a defibrillation port configured to guide via electrodes the electrical charge to the person;
a first wireless communication module configured to establish a wireless communication link with the second communication module, the first communication module being further adapted to receive wirelessly a data signal transmitted by the second communication module over the communication link, the data signal encoding the resuscitation event data stored in the transmitting device;
a memory configured to store the resuscitation event data that has been decoded from the data signal;
a processor configured to monitor a reception parameter of the communication link while the data signal is being received, and to set an alert flag if the processor determines from the reception parameter that reception of the data signal may be discontinued prematurely; and
a user interface configured to output an alerting user notification responsive to the alert flag being set, in which
the reception parameter includes a rate of change of an Error Correction Rate (ECR) from correcting errors as the resuscitation event data is decoded from the data signal, and
the alert flag is set if the rate of change crosses a threshold.

10. The external defibrillator of claim 9, in which
the user interface is further capable of outputting a regular user notification different from the alerting user notification that the data signal is being received.

11. The external defibrillator of claim 9, in which
the alerting user notification is at least one of a visual, audio, or physical notification.

12. The external defibrillator of claim 9, in which
the alerting user notification further includes a suggestion that a user check whether the transmitting device has been moved away from the defibrillator.

13. The external defibrillator of claim 9, in which
the alerting user notification further includes a suggestion that a user check for a potential source of interference with the communication link.

14. The external defibrillator of claim 9, in which
the processor is further configured to reset the alert flag if the processor determines from the reception parameter that the reception of the data signal has been restored.

15. The external defibrillator of claim 14, in which
the user interface is further capable of outputting a regular user notification different from the alerting user notification that the data signal is being received responsive to the determination that the reception of the data signal has been restored.

16. The external defibrillator of claim 9, in which
the transmitting device is a second external defibrillator distinct from the defibrillator.

17. An external defibrillator for defibrillating a person, and for receiving resuscitation event data from a transmitting device distinct from the external defibrillator, the transmitting device including a second housing and a second wireless communication module, the external defibrillator comprising:
a first housing;
an energy storage module in an interior of the first housing configured to store an electrical charge;
a defibrillation port configured to guide via electrodes the electrical charge to the person;
a first wireless communication module configured to establish a wireless communication link with the second communication module, the first communication module being further adapted to receive wirelessly a data signal transmitted by the second communication module over the communication link, the data signal encoding the resuscitation event data stored in the transmitting device;
a memory configured to store the resuscitation event data that has been decoded from the data signal;
a processor configured to monitor a reception parameter of the communication link while the data signal is being received, and to set an alert flag if the processor determines from the reception parameter that reception of the data signal may be discontinued prematurely; and
a user interface configured to output an alerting user notification responsive to the alert flag being set, in which
the processor is further configured to:
determine an expected amount of time needed for the first communication module to fully receive the data signal; and
determine an expected amount of time remaining before the receiving of the data signal becomes discontinued.

18. The external defibrillator of claim 17, in which
the processor is configured to determine the expected amount of time needed for the first communication module to fully receive the data signal by determining an amount of data remaining to be received.

19. The external defibrillator of claim 17, in which
the processor is configured to determine the expected amount of time remaining before the receiving of the data signal becomes discontinued by determining a degradation rate of the communication link.

20. The external defibrillator of claim 17, in which
the processor is configured to not set the alert flag if the processor determines that the expected amount of time needed for the first communication module to fully receive the data signal is less than the expected amount of time remaining before the receiving of the data signal becomes discontinued.

21. The external defibrillator of claim 17, in which
the alerting user notification is structured to convey the expected amount of time needed for the first communication module to fully receive the data signal, or the expected amount of time remaining before the receiving of the data signal becomes discontinued, or both, to a user.

22. The external defibrillator of claim 17, in which
the user interface is further capable of outputting a regular user notification different from the alerting user notification that the data signal is being received.

23. The external defibrillator of claim 17, in which
the alerting user notification is at least one of a visual, audio, or physical notification.

24. The external defibrillator of claim 17, in which
the alerting user notification further includes a suggestion that a user check whether the transmitting device has been moved away from the defibrillator.

25. The external defibrillator of claim 17, in which the alerting user notification further includes a suggestion that a user check for a potential source of interference with the communication link.

26. The external defibrillator of claim 17, in which the processor is further configured to reset the alert flag if the processor determines from the reception parameter that the reception of the data signal has been restored.

27. The external defibrillator of claim 26, in which the user interface is further capable of outputting a regular user notification different from the alerting user notification that the data signal is being received responsive to the determination that the reception of the data signal has been restored.

28. The external defibrillator of claim 17, in which the transmitting device is a second external defibrillator distinct from the defibrillator.

* * * * *

UNITED STATES PATENT AND TRADEMARK OFFICE
CERTIFICATE OF CORRECTION

| | | |
|---|---|---|
| PATENT NO. | : 8,676,312 B2 | Page 1 of 1 |
| APPLICATION NO. | : 13/284610 | |
| DATED | : March 18, 2014 | |
| INVENTOR(S) | : John Carlton Daynes et al. | |

It is certified that error appears in the above-identified patent and that said Letters Patent is hereby corrected as shown below:

In the Specification

Column 1, lines 14-15, "[SER_NO_OF.sub.--7257-0036/P40442.01]" should be replaced with --13/191,320--.

Column 1, lines 20-21, "[SER_NO_OF.sub.--7257-0039/P40442.02]" should be replaced with --13/191,334--.

Signed and Sealed this
Twelfth Day of August, 2014

Michelle K. Lee
*Deputy Director of the United States Patent and Trademark Office*